US011432740B2

(12) United States Patent
Oren et al.

(10) Patent No.: US 11,432,740 B2
(45) Date of Patent: Sep. 6, 2022

(54) INTRODUCER SHEATH LOCALIZATION AND VISUALIZATION

(71) Applicant: ST. JUDE MEDICAL, CARDIOLOGY DIVISION, INC., St. Paul, MN (US)

(72) Inventors: Eitan Oren, Haifa (IL); Oded Sudarsky, Kar Yedidya (IL); Adar Shlain, Hadar-Am (IL); Stavit Cohen, Kerem Maharal (IL)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 423 days.

(21) Appl. No.: 16/448,728

(22) Filed: Jun. 21, 2019

(65) Prior Publication Data

US 2020/0000367 A1   Jan. 2, 2020

Related U.S. Application Data

(60) Provisional application No. 62/691,026, filed on Jun. 28, 2018.

(51) Int. Cl.
| | |
|---|---|
| A61B 5/00 | (2006.01) |
| A61B 5/06 | (2006.01) |
| A61B 34/20 | (2016.01) |
| A61B 18/14 | (2006.01) |
| A61M 25/01 | (2006.01) |
| A61B 18/00 | (2006.01) |

(52) U.S. Cl.
CPC .............. *A61B 5/063* (2013.01); *A61B 5/068* (2013.01); *A61B 34/20* (2016.02); *A61B 18/1492* (2013.01); *A61B 2018/00577* (2013.01); *A61B 2034/2051* (2016.02); *A61M 25/01* (2013.01)

(58) Field of Classification Search
CPC ...... A61B 18/1492; A61B 2017/00053; A61B 2017/00243; A61B 2018/00577; A61B 2018/00678; A61B 2018/00839; A61B 2018/00875; A61B 2018/1467; A61B 2018/1475; A61B 2034/105; A61B 2034/2051; A61B 2034/2053; A61B 2090/0811; A61B 2090/376; A61B 34/20; A61B 34/25; A61B 5/062; A61B 5/063; A61B 5/068; A61B 90/37; A61M 25/01
See application file for complete search history.

(56) References Cited

U.S. PATENT DOCUMENTS

| | | |
|---|---|---|
| 6,233,476 B1 | 5/2001 | Strommer et al. |
| 6,498,944 B1 | 12/2002 | Ben-Haim et al. |
| 6,690,963 B2 | 2/2004 | Ben-Haim et al. |
| 6,788,967 B2 | 9/2004 | Ben-Haim et al. |
| 7,197,354 B2 | 3/2007 | Sobe |
| 7,263,397 B2 | 8/2007 | Hauck et al. |
| 7,386,339 B2 | 6/2008 | Strommer et al. |
| 7,848,789 B2 | 12/2010 | Govari et al. |
| 8,265,745 B2 | 9/2012 | Hauck et al. |
| 9,026,196 B2 | 5/2015 | Curran et al. |
| 9,326,702 B2 | 5/2016 | Eichler et al. |
| 9,848,832 B2 | 12/2017 | Oren et al. |
| 9,901,303 B2 | 2/2018 | Olson |

(Continued)

*Primary Examiner* — Mark D Remaly
(74) *Attorney, Agent, or Firm* — Dykema Gossett PLLC (57) ABSTRACT

Aspects of the present disclosure are directed to the localization of an introducer sheath relative to an intravascular catheter. Further embodiments of the present disclosure are directed to the visualization of the introducer sheath on a graphical user interface of a navigation system.

15 Claims, 6 Drawing Sheets

(56) References Cited

U.S. PATENT DOCUMENTS

2013/0066193 A1   3/2013   Olson
2016/0324441 A1   11/2016  Mosesov et al.
2017/0164870 A1   6/2017   Byrd

INTRODUCER SHEATH LOCALIZATION AND VISUALIZATION

CROSS-REFERENCE TO RELATED APPLICATIONS

This application claims the benefit of U.S. provisional application No. 62/691,026, filed 28 Jun. 2018, which is hereby incorporated by reference as though fully set forth herein.

BACKGROUND a. Field

The present disclosure relates generally to mapping and visualization of medical instruments within a human body. More specifically, the mapping and visualization of introducer sheaths relative to intravascular catheters.

b. Background Art

Electrophysiology (EP) catheters have been used for an ever-growing number of procedures. For example, EP catheters have been used for diagnostic, therapeutic, mapping and ablative procedures, to name just a few examples. Typically, a catheter is manipulated through a patient's vasculature to an intended site, for example, a site within the patient's heart, and carries one or more electrodes, which may be used for diagnosis, mapping, ablation, or other treatments. Precise positioning of the catheters and clinician knowledge of the precise location within the body of the patient is desirable for improved efficacy.

To position a catheter within the body at a desired site, some type of navigation must be used, such as using mechanical steering features incorporated into the catheter (and/or into an introducer sheath). To determine the relative position of the catheter to patient anatomy, navigation systems (also referred to as localization systems) have been developed. Once the catheter is positioned within the patient as desired, a clinician may diagnose a patient's cardiac conditions, such as atrial fibrillation (or other cardiac arrhythmia), and facilitate a clinician's determination of a treatment regimen. EP catheters may further deliver an ablation therapy (e.g., RF ablation energy) to treat symptoms related to, for example, a cardiac arrhythmia.

The foregoing discussion is intended only to illustrate the present field and should not be taken as a disavowal of claim scope.

BRIEF SUMMARY

Aspects of the present disclosure are directed to the mapping and visualization of medical instruments within a human body. More specifically, the mapping and visualization of introducer sheaths relative to intravascular catheters. In some embodiments, the instant disclosure relates to the localization of an introducer sheath relative to a distal tip of an EP catheter, and the visualization of the EP catheter and the introducer sheath on a graphical user interface.

Some embodiments are directed to a system for visualizing an introducer sheath location within the body, the system including controller circuitry. The controller circuitry receives electrical signals from one or more electrodes on an electrophysiology catheter indicative of a position and orientation of a distal end of the catheter and a position of an introducer sheath relative to the catheter. Based on the received electrical signals, the controller circuitry determines the position and orientation of the distal end of the catheter and the position of the introducer sheath relative to the catheter. The controller circuitry further generates an image for a display that visualizes states indicative of the relative locations of the catheter and the introducer sheath. The visualization states include: a first visualization state where the visual indicator of the introducer sheath is proximal a proximal-most electrode of the plurality of electrodes, a second visualization state where the visual indicator of the introducer sheath is disposed over at least one of the plurality of electrodes of the catheter, and a third visualization state where the visual indicator of the introducer sheath covers each of the one or more electrodes on the catheter. In more specific embodiments, the controller circuitry determines the position of the introducer sheath relative to the catheter by: determining a baseline impedance of the one or more electrodes outside of an introducer sheath, monitoring the impedance of the electrodes during an operation, determining whether the impedance of the one or more electrodes exceeds the baseline impedance, and generating the image for the display including the introducer sheath in one of the three visualization states based on the determined impedance of the one or more electrodes relative to the baseline impedance.

Some embodiments of the present disclosure are directed to a system for detecting and visualizing a location of an introducer sheath, the system including the introducer sheath, a catheter, controller circuitry, and a display. The introducer sheath navigates a patient vasculature. The catheter includes one or more electrodes, and is delivered to a target region within the vasculature via a lumen within the introducer sheath. The controller circuitry is communicatively coupled to the one or more electrodes, and determines a position of the catheter within the patient based on electrical signals received from the one or more electrodes on the catheter. The controller circuitry further determines an approximate position of the introducer sheath based on the electrical signals received from the one or more electrodes on the catheter, and generates an image for a display that visualizes the relative locations of the catheter and the introducer sheath. The display, communicatively coupled to the controller circuitry, displays the generated image to a clinician to assist in diagnostic and therapeutic intravascular procedures. In yet further more specific embodiments, the controller circuitry determines the position of the introducer sheath relative to the catheter by determining a baseline impedance of the one or more electrodes outside of an introducer sheath, and monitors the impedance of the electrodes during an operation. When the impedance of one or more of the electrodes exceeds a threshold, the one or more electrodes are determined to be in contact with an inner wall of the catheter sheath.

Various embodiments of the present disclosure are directed to methods of visualizing an introducer sheath location. One such method includes receiving data indicative of a position and orientation of a distal end of a catheter and a position of the introducer sheath relative to the catheter from one or more electrodes positioned near a distal end of the catheter. The position of the catheter is then determined, followed by the position of the introducer sheath relative to the catheter. An image is generated for a display that visualizes the relative locations of the catheter and the introducer sheath, and the image is displayed to a clinician to facilitate intravascular positioning of the catheter, diagnostics and therapy. In specific embodiments, the method step of determining the position of the introducer sheath relative to the catheter further includes determining a baseline impedance of the one or more electrodes outside of an introducer sheath, and monitoring the impedance of the electrodes during an operation. When the impedance of one or more of the electrodes exceeds a threshold, the one or more electrodes are determined to be in contact with an inner wall of the catheter sheath.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings, in which.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

Aspects of the present disclosure are directed to the mapping and visualization of medical instruments within a human body (e.g., vasculature). More specifically, aspects of the present disclosure are directed to the mapping and visualization of introducer sheaths relative to intravascular catheters. For example, the localization of an introducer sheath relative to a distal tip of an electrophysiology catheter, and the visualization of the electrophysiology catheter and the introducer sheath on a graphical user interface (GUI).

Some embodiments of the present disclosure are directed to intravascular catheters for both electrophysiology mapping and ablation. These catheters may be used to detect electrophysiological characteristics of tissue in contact with the electrodes, and conduct therapeutic ablations of the tissue. In particular, the instant disclosure relates to both linear, planar, basket-type end effectors, among others, as (partially) delivered to a target location within a patient's vasculature via an introducer sheath.

In some specific aspects of the present disclosure, a planar array catheter may be used, for example, to diagnose and treat a cardiac arrhythmia. Many cardiac arrhythmias are triggered by stray electrical signals emanating from one or more of the pulmonary veins. To reach the left atrium of the cardiac muscle, where these stray electrical signals may originate, a transseptal approach may be used. The transseptal approach and puncture of the fossa ovalis is typically conducted using an introducer sheath. After the puncture of the fossa ovalis is complete, a distal end of the sheath may then be anchored to the fossa ovalis and a catheter may be extended through the sheath to conduct electrophysiology mapping within the left atrium, ablate myocardial tissue in proximity to the pulmonary veins to alleviate symptoms related to atrial fibrillation, and re-map the left atrium to verify the efficacy of the therapy. During such intravascular procedures, it is desirable for a clinician to understand the relative position of a distal end of the introducer sheath relative to an end effector of a catheter extending through the sheath. For example, a clinician may not wish to effect steering inputs on the end effector until it has fully exited the distal end of the sheath. As yet another example, a clinician may wish to implement a first bend with the introducer sheath and a second bend with the catheter, requiring positional knowledge of the sheath and catheter relative to one another. Aspects of the present disclosure determine and visualize, for the clinician (via a graphical user interface or GUI), the approximate location of a distal end of the introducer sheath relative to an end effector of the catheter.

Once an end effector of a catheter has fully exited a distal end of the introducer sheath, the end effector may be positioned into contact with the cardiac muscle to conduct a pacing procedure, and/or ablation therapy. During the pacing procedure, adjacent electrodes are assigned to bipole pairings, and each bipole pair samples the electrical characteristics of the tissue between the pair. The resulting electrical signals are received and processed by controller circuitry. The controller circuitry develops an electrophysiology map by associating the sampled signal from each bipole pair with a location of the tissue sampled. The electrogram from each bipole pair may be analyzed and various electrical characteristics may be visually indicated on an electrophysiology map by color-coding (or other visual indication scheme, e.g., shading, patterning, etc.). The pacing and resulting electrophysiology mapping may be conducted pre and post ablation to verify the efficacy of the therapy. Before de-anchoring the introducer sheath from the transseptal wall at the conclusion of the operation, aspects of the present disclosure are directed to visually confirming through a GUI that the end effector of the catheter has been fully retracted into the sheath before retracting the sheath back through the vasculature of the patient.

Details of the various embodiments of the present disclosure are described below with specific reference to the figures.

Figure 1:
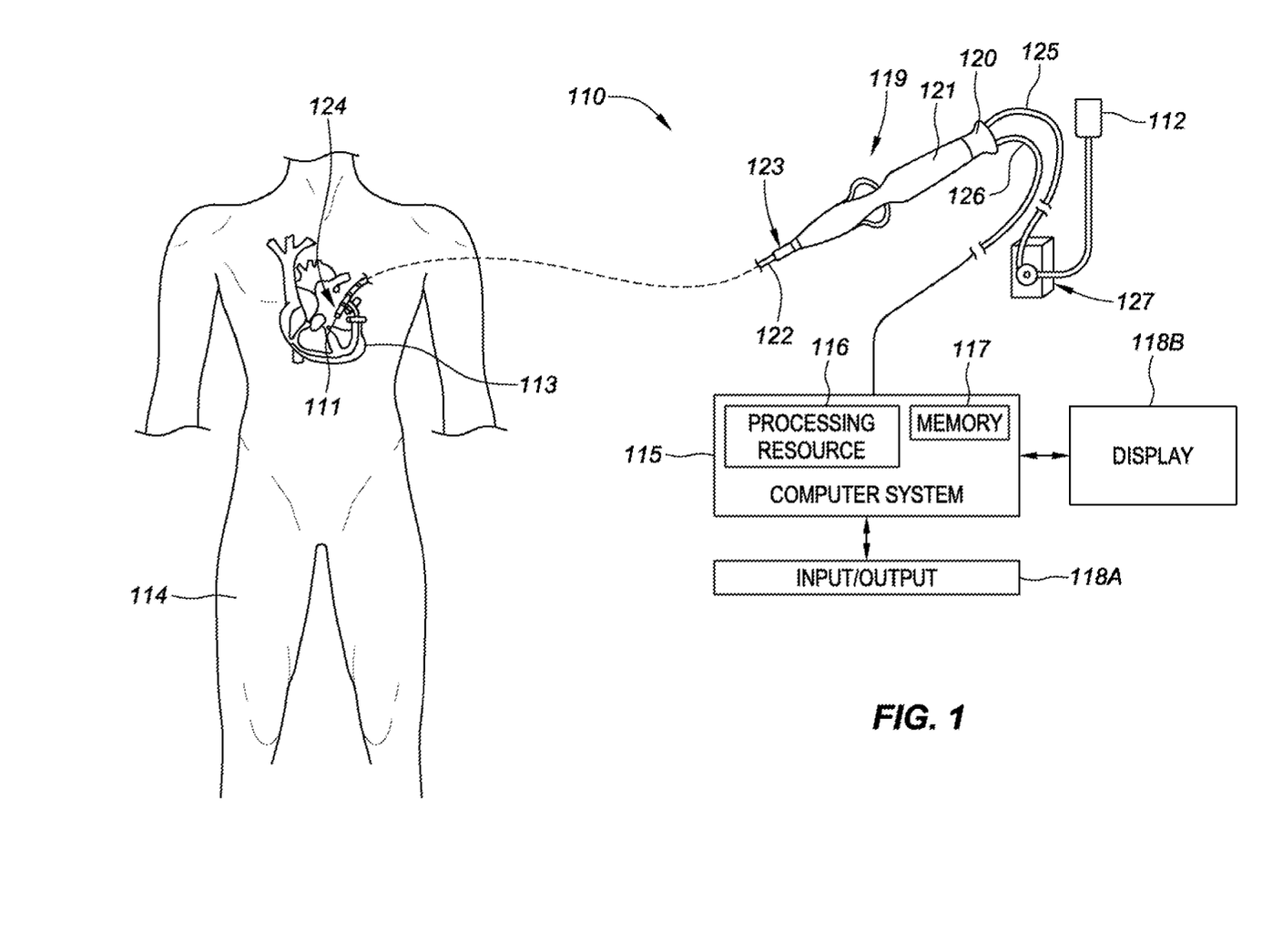
FIG. 1 is a diagrammatic overview of an intravascular catheter system, consistent with various embodiments of the present disclosure.

FIG. 1 is a diagrammatic overview of an intravascular catheter system 110, consistent with various embodiments of the present disclosure. The system includes an elongated medical device 119 that includes an end effector 111 for electrophysiological diagnostics, visualization, and/or therapy of tissue 113 (such as cardiac or other tissue) in the body. For example, the medical device 119 may be used for ablation therapy of tissue 113 or mapping purposes in a patient's body 114. FIG. 1 further shows various subsystems included in the overall system 110. The system 110 may include a main computer system 115 (including an electronic control unit 116 and data storage 117, e.g., memory). The computer system 115 may further include conventional interface components, such as various user input/output mechanisms 118A and a display 118B, among other components. Information provided by the end effector 111 may be processed by the computer system 115 and may provide data to the clinician via the input/output mechanisms 118A and/or the display 118B. As pertinent herein, the display may visualize the location of the end effector 111 relative to an introducer sheath.

In the illustrative embodiment of FIG. 1, the elongated medical device 119 may include a cable connector or interface 120, a handle 121, a tubular body or shaft 122 having a proximal end 123 and a distal end 124. The elongated medical device 119 may also include other conventional components not illustrated herein, such as a temperature sensor, additional electrodes, and corresponding conductors or leads. The connector 120 may provide mechanical, fluid and/or electrical connections for cables 125, 126 extending from a fluid reservoir 112 and a pump 127 and the computer system 115, respectively. The connector 120 may comprise conventional components known in the art and, as shown, may be disposed at the proximal end of the elongated medical device 119.

The handle 121 facilitates a user to grasp or hold the elongated medical device 119 and may further provide a mechanism for steering or guiding the shaft 122 within the patient's body 114. For example, the handle 121 may include a mechanism configured to change the tension on a pull-wire extending through the elongated medical device 119 to a distal end 124 of the shaft 122 or some other mechanism to steer the shaft 122. The handle 121 may be conventional in the art, and it will be understood that the configuration of the handle 121 may vary. Though not shown in the system 110, the elongated medical device 119 may be delivered to tissue 113 via an introducer sheath (as discussed in more detail below).

The computer system 115 may utilize software, hardware, firmware, and/or logic to perform a number of functions described herein. The computer system 115 may be a combination of hardware and instructions to share information. The hardware, for example may include processing resource 116 (e.g., controller circuitry) and/or a memory 117 (e.g., non-transitory computer-readable medium (CRM) database, etc.). A processing resource 16, as used herein, may include a number of processors capable of executing instructions stored by the memory resource 117. Processing resource 116 may be integrated in a single device or distributed across multiple devices. The instructions (e.g., computer-readable instructions (CRI)) may include instructions stored on the memory 117 and executable by the processing resource 116 for conducting ablation therapy, pacing, and/or electrophysiology mapping of the tissue 113.

The memory resource 117 is communicatively coupled with the processing resource 116. A memory 117, as used herein, may include a number of memory components capable of storing instructions that are executed by processing resource 116. Such a memory 117 may be a non-transitory computer readable storage medium, for example. The memory 117 may be integrated in a single device or distributed across multiple devices. Further, the memory 117 may be fully or partially integrated in the same device as the processing resource 116 or it may be separate but accessible to that device and the processing resource 116. Thus, it is noted that the computer system 115 may be implemented on a user device and/or a collection of user devices, on a mobile device and/or a collection of mobile devices, and/or on a combination of the user devices and the mobile devices.

The memory 117 may be communicatively coupled with the processing resource 116 via a communication link (e.g., path). The communication link may be local or remote to a computing device associated with the processing resource 116. Examples of a local communication link may include an electronic bus internal to a computing device where the memory 117 is one of a volatile, non-volatile, fixed, and/or removable storage medium in communication with the processing resource 116 via the electronic bus.

Cardiac Mapping Systems are capable of displaying a three-dimensional (3D) position of electrophysiology catheters within an overlaid model or image of a cardiac chamber the catheter is disposed therein. These mapping systems may also display cardiac electrical activity as waveform traces and as dynamic 3-D isopotential maps on the model of the cardiac chamber. The contoured surfaces of these three dimensional models are based on the anatomy of the patient's own cardiac chamber. These mapping systems may use impedance-based, magnetic-based, or a hybrid-type localization systems to render catheter position within the cardiac model. Aspects of the present disclosure are directed to the determination of introducer sheath position along a longitudinal axis shared with the catheter, without the need for additional position sensing element(s) on the introducer sheath.

Figure 2A:
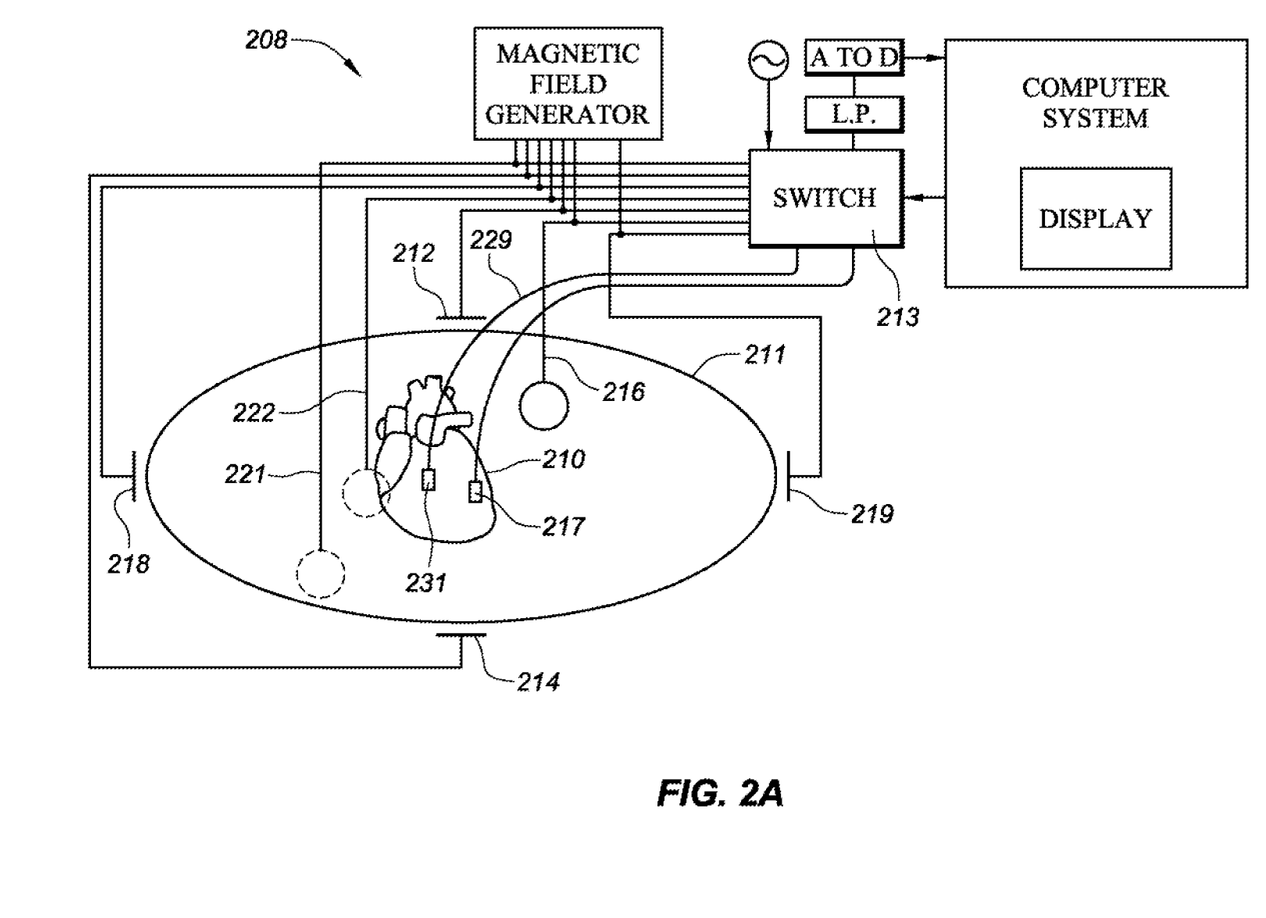
FIG. 2A is a schematic diagram of an intravascular catheter mapping system, consistent with various embodiments of the present disclosure.

FIG. 2A shows a schematic diagram of a navigation system 208 used for navigating the anatomy of a patient 211 (depicted, for simplicity sake, as an oval in FIG. 2A) during a medical procedure. For example, as shown in FIG. 2A, the system 208 may be used to map a cardiac muscle 210, and to navigate a cardiac catheter through the chambers of the heart. The navigation system 208 determines the location (and, in some aspects, the orientation) of objects (e.g., a portion of a diagnostic or ablation catheter, such as the electrode assembly 312 depicted in FIGS. 3A and 3B), typically within a three dimensional space, and expresses those locations as position information determined relative to at least one reference. The navigation system 208 may be used to determine the location of the cardiac catheter within a magnetic field, which is then overlaid onto, for example, an image or a model of the cardiac muscle 210. In other embodiments, magnetic resonance imaging data, among other reference data may be overlaid onto the three-dimensional space to provide a clinician with a virtual work environment in which to reference for real-time position of the cardiac catheter relative to the cardiac muscle 210.

The navigation system 208 may include various visualization, mapping, and navigation components. For example, the navigation system 208 may comprise a magnetic field based system such as the CARTO™ system commercially available from Biosense Webster, and as generally shown with reference to one or more of U.S. Pat. Nos. 6,498,944; 6,788,967; and 6,690,963, the disclosures of which are hereby incorporated by reference in their entireties as though fully set forth herein.

In another example embodiment, the navigation system 210 may comprise a magnetic field based system such as the MEDIGUIDE™ system available from St. Jude Medical, Inc., and as generally shown with reference to one or more of U.S. Pat. Nos. 6,233,476; 7,197,354; 7,386,339; and U.S. patent application Ser. No. 14/208,120 entitled "Medical Device Navigation System" filed on 13 Mar. 2014. These disclosures are hereby incorporated by reference in their entireties as though fully set forth herein.

The navigation system 208 may also comprise an impedance-based system such as ENSITE™ NAVX™ System, each from Abbott. In such an embodiment, 216, 221, and 222 may be electrode patches attached to the outer surface of the patient's body to sense a change of impedance as an intravascular catheter is maneuvered through the patient's vasculature. The measured impedance change at each of the patches may then be used to triangulate the position of the catheter there between. In yet other embodiments, the navigation system 210 may be an electrical-impedance based system, such as an EnSite™ Velocity™ system running a version of EnSite™ NavX™ software commercially available from St. Jude Medical, Inc., and as also shown generally by reference to U.S. patent application Ser. No. 10/819,027 (issued as U.S. Pat. No. 7,263,397), hereby incorporated by reference in its entirety as though fully set forth herein. Some embodiments of the navigation system may include a sensor for producing signals indicative of catheter location and/or distal portion orientation information, and can include, for example, one or more electrodes in the case of an impedance-based localization system such as the EnSite™ Velocity™ system running EnSite™ NavX™ software. These electrodes may already exist in some instances, or alternatively, one or more coils (i.e., wire windings) configured to detect one or more characteristics of a low-strength magnetic field, for example, in the case of a magnetic-field based localization system such as one including the MEDIGUIDE™ Technology described above.

In yet another embodiment, the navigation system 208 may comprise a hybrid impedance-based and magnetic-based system, such as, for example and without limitation, the systems described in pending U.S. patent application Ser. No. 13/231,284 entitled "Catheter Navigation Using Impedance and Magnetic Field Measurements" filed on 13 Sep. 2011 and U.S. patent application Ser. No. 13/087,203 entitled "System and Method for Registration of Multiple Navigation Systems to a Common Coordinate Frame" filed on 14 Apr. 2011, U.S. patent application Ser. No. 15/380,786 entitled "Motion Box Visualization for Electromagnetic Sensor Tracking System" filed on 15 Dec. 2016, and U.S. Pat. No. 9,848,832, each of which is hereby incorporated by reference in its entirety as though set fully forth herein. Examples of hybrid impedance-based and magnetic-based systems include the ENSITE™ PRECISION™ system commercially available from Abbott, or the CARTO™ 3 system commercially available from Biosense Webster (e.g., as exemplified by U.S. patent application Ser. No. 12/425,778 (issued as U.S. Pat. No. 7,848,789), which is hereby incorporated by reference in its entirety as though fully set forth herein). In yet still other embodiments, the navigation system 208 may comprise or be used in conjunction with other commonly available systems, such as, for example and without limitation, fluoroscopic, computed tomography (CT), and magnetic resonance imaging (MRI)-based systems. For purposes of clarity and illustration only, the navigation system 208 will be described hereinafter as comprising a magnetic-based system.

For ease of description, the remainder of this disclosure will be with respect to one or more types of navigation systems, but the systems, methods, and techniques discussed herein are not so limited. Instead, the systems, methods, and techniques discussed herein may also find application with another type of navigation system, including, but not limited to, those systems and types of systems noted above.

FIG. 2A may further exemplify a hybrid navigation system 208 including two localization systems: an impedance-based localization system and a magnetic-based localization system.

In general, and as shown in FIG. 2A, a navigation system (utilizing magnetic-based localization) includes a plurality of magnetic field transmitters (e.g., 212, 214, 216, 218, 219, and 221) which emit one or more magnetic fields across the patient's body 211. These magnetic field transmitters, which may be placed upon or attached/applied to the patient, or fixed to an external apparatus, define three generally orthogonal axes (e.g., x-axis, y-axis, and z-axis). The magnetic field transmitters are electrically coupled to a magnetic field generator. The magnetic field generator generates one or more magnetic fields that may be transmitted simultaneously, time multiplexed, and/or frequency multiplexed. A switch 213 samples the signals received from one or more of receivers 217, 231 (e.g., a catheter, patient reference sensor, internal reference sensor, etc.). The signals received from the receivers are indicative of the magnetic field that traversed through the patient's body 211 from one or more of the transmitters. The received signals are then converted from an analog to a digital signal for further processing by the computer system. The computer system performs computations on the data received from the receivers to determine, for example, the location of a cardiac catheter within the heart 210.

For reference by a clinician during an electrophysiology procedure, the perceived location of the catheter within the magnetic field is presented on a display in relation to known reference points (e.g., cardiac chambers, arteries, etc.).

A magnetic-based navigation system 208 may include a fixed reference 222 to define the origin of the magnetic-based mapping system's coordinate frame. This fixed reference provides a relative position to which the positions of receivers 217, 231 on the catheter are measured. A fixed reference can likewise be in a fixed internal or external location. Likewise, multiple references may be used for the same or different purposes (e.g., to correct for respiration, patient shift, system drift, or the like).

A computer system (or controller circuitry), which can comprise a conventional general-purpose computer, a special-purpose computer, a distributed computer, or any other type of computer, and which can comprise one or more processors, such as a single central processing unit (CPU), or a plurality of processing units, commonly referred to as a parallel processing environment, may control navigation system 208 and/or execute instructions to practice the various aspects of the embodiments described herein.

Figure 2B:
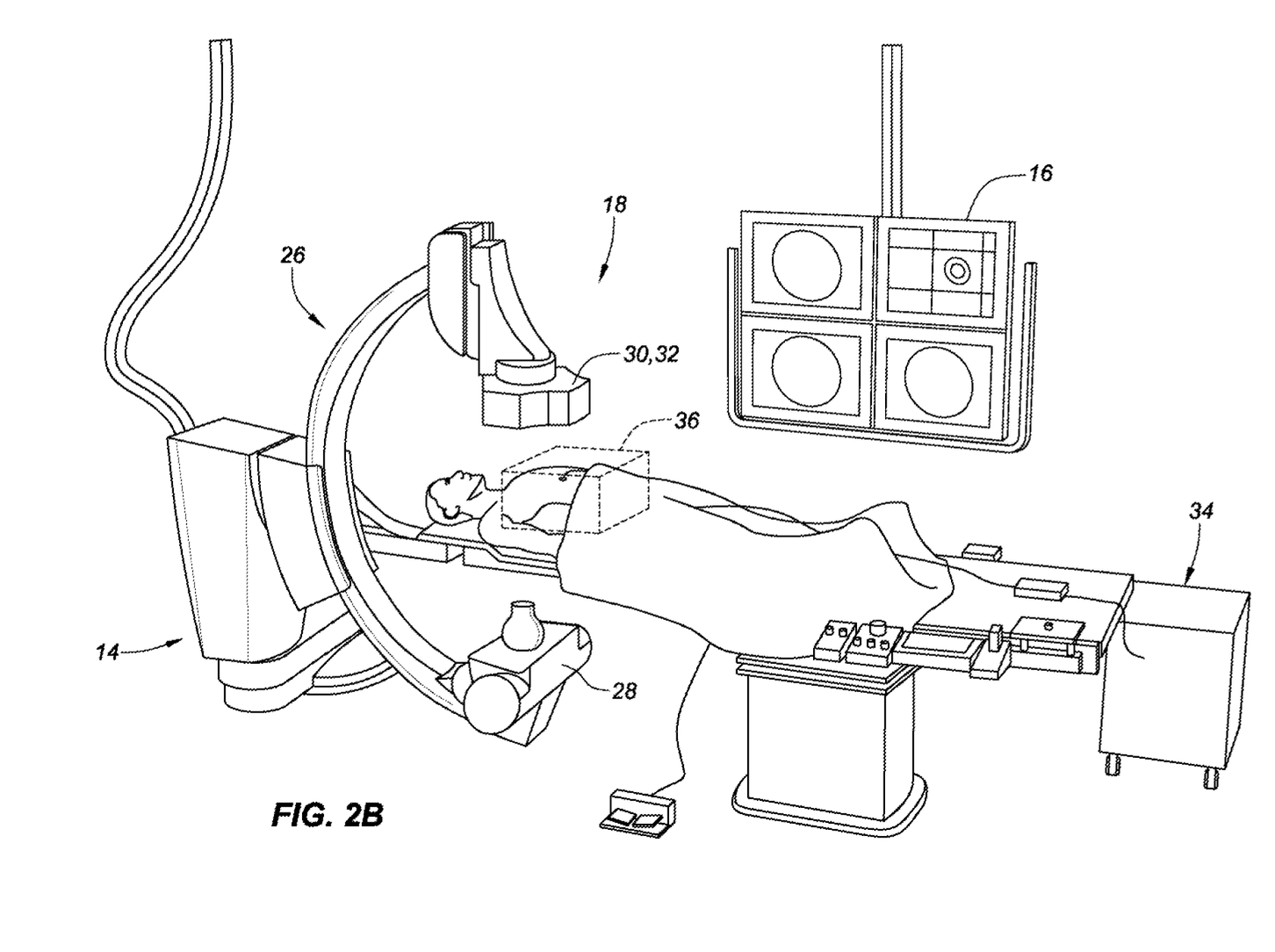
FIG. 2B is a diagrammatic view of an embodiment of an electrophysiology laboratory including a fluoroscopic imaging system and a magnetic field-based positioning system, consistent with various embodiments of the present disclosure.

FIG. 2B is a diagrammatic view of an embodiment of a medical device laboratory including a medical imaging system 14 (shown as a fluoroscopic imaging system) and a magnetic field-based navigation system 18.

The imaging system 14 may include a C-arm 26, an imaging radiation transmitter 28, and an imaging radiation detector 30. The C-arm 26 may be rotated and/or translated and radiation (i.e., x-ray) may be transmitted from the imaging radiation transmitter 28 to the imaging radiation detector 30 to image an area of interest of a the body of a patient. In an embodiment, the area of interest may be or may include the heart and/or another organ of the patient. The imaging system 14 may provide images to a control unit for further processing.

With continued reference to FIG. 2B, the navigation system 18 may include a magnetic transmitter assembly (MTA) 32 and a magnetic processing core 34 for determining position and orientation (P&O) readings. In an embodiment, the processing core 34 may be a part of a control unit. The MTA 32 may be configured to generate one or more magnetic fields in and around a volume of interest 36, such as the patient's chest cavity, in a predefined three-dimensional space. Magnetic field sensors coupled with a medical device may be configured to sense one or more characteristics of the magnetic field(s) and, when the sensors are in the volume of interest 36, may each generate a respective signal that is provided to the magnetic processing core 34. The processing core 34 may be responsive to these detected signals and may calculate respective three-dimensional position and orientation readings for each magnetic field sensor in the volume of interest 36. Thus, the navigation system 18 may enable real-time tracking of each magnetic field sensor in three-dimensional space. The position of the sensors may be shown on the display 16 relative to, for example, real-time images obtained from the medical imaging system 14, and/or a model of the heart or other features of the volume of interest 36.

Figures 3A, 3B:
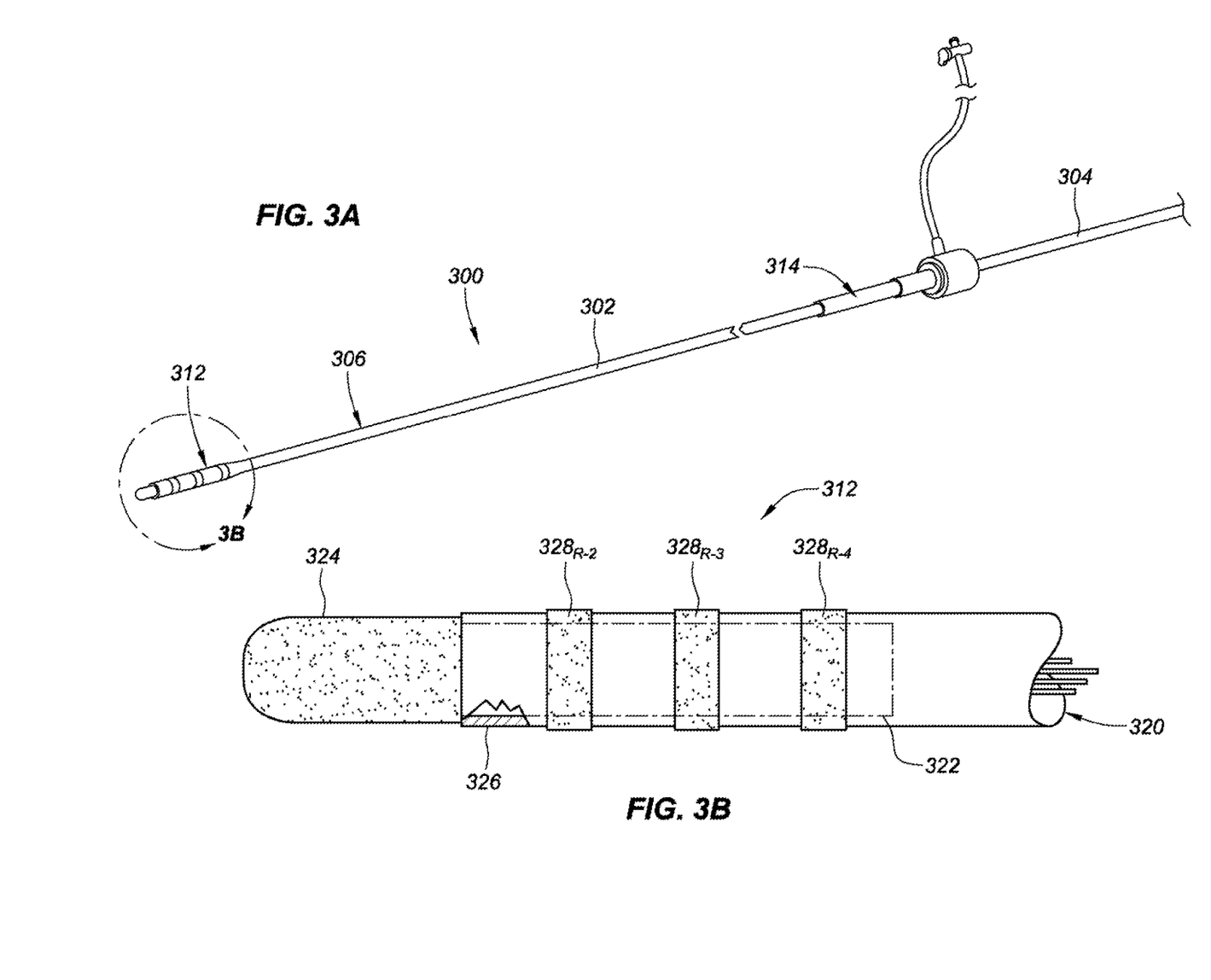
FIG. 3A is an isometric view of a catheter assembly comprising a catheter configured for localization in a magnetic mapping system and an introducer, consistent with various embodiments of the present disclosure.
FIG. 3B is an enlarged side view of the distal tip assembly of the catheter of FIG. 3A, consistent with various embodiments of the present disclosure.

FIG. 3A is a simplified, isometric view of a single-use catheter assembly 300, comprising a catheter 306 that includes a catheter tip assembly (or an electrode assembly, or distal tip assembly) 312 at a distal end portion and operatively adapted for conducting a diagnostic and/or a therapeutic procedure under clinician control. A proximal end portion 304 of the catheter 306 may include a steering handle or other mechanism (not shown). In the present embodiment, catheter 306 is a mapping catheter. The catheter 306 includes a flexible shaft 302 extending between the proximal end portion 304 and the catheter tip assembly 312. The catheter assembly 300 further includes an electrical connector (not shown) configured to establish electrical connection(s) between the catheter tip assembly 312 and external electrical apparatus (not shown) to perform, for example, localization, mapping, ablation, and/or pacing procedures. FIG. 3A further shows an introducer sheath 314 comprising part of the catheter assembly 300. The catheter tip assembly 312 may comprise a plurality of localization coils. These localization coils may be located, for example, in the region shown by the dashed box 322 in FIG. 3B.

FIG. 3B is an enlarged, side view showing, in greater detail, the tip assembly 312. The tip assembly 312 includes a tip electrode 324, a plurality of ring electrodes $328_{R-2}$, $328_{R-3}$, and $328_{R-4}$, and a plurality of electrical conductors 320 (e.g., one conductor electrically connected to each of the three ring electrodes and a separate conductor electrically connected to the tip electrode 324). Additional electrical connectors may extend proximally from the tip assembly 312 if localization coils are located in, for example, the area outlined by dashed box 322. In some embodiments, the electrodes may be capable of electrophysiology mapping, RF tissue ablation, and facilitating localization in an impedance or hybrid-based catheter navigation system (e.g., MediGuide™ System, and/or EnSite™ NavX™ System, each from Abbott). In some specific embodiments, some of the electrodes may be multi-purpose, while other electrodes are single-purpose. For example, some of the electrodes may function as both navigation, ablation, and electrophysiology mapping electrodes, while others may function only as electrophysiology mapping electrodes, and yet other electrodes may function only as navigation electrodes.

In various embodiments of the present disclosure, distal tip electrodes (e.g., tip electrode 324, a plurality of ring electrodes $328_{R-2}$, $328_{R-3}$, and $328_{R-4}$) of the catheter tip assembly 312, during insertion and withdrawal of the catheter, may be monitored to determine if the catheter is within introducer sheath 314. The sensed impedance at the distal tip electrodes will vary depending upon whether the electrodes are contacting an inner wall of the sheath, a blood pool within the cardiac muscle and/or myocardial tissue. The electrodes may be independently monitored to determine the extent to which the catheter is extending out of the introducer sheath.

Various embodiments of the present disclosure may rely upon the Abbott EnSite Precision™ navigation system, where the EnSite™ navigation system provides real-time tracking of a catheter end effector, via electrodes thereon, placed within a target region of the patient's vasculature. One or more of these electrodes may be multi-function electrodes (e.g., capable of both tissue ablation, electrophysiological diagnostics, and/or tracking-impedance and/or magnetic-based). The system may further identify which electrodes are un/covered by an introducer sheath and thereby the relative co-linear position of an end-effector of the catheter relative to a distal end of the introducer sheath. As a result, the system may then visualize in a GUI the relative position of the distal end of the introducer sheath, as well as the end effector of the catheter (without needing to add cost to the introducer sheath by adding localization sensors thereto).

In some embodiments consistent with the present disclosure, sheath detection may be based on the comparison of electrodes' current impedance readings to baseline readings for the respective electrodes. Baseline collection of impedance readings for each of the electrodes may be initiated by a user (prior to an operation, for example). The baseline impedance readings may be collected while all electrodes are out of the introducer sheath. During sheath detection, each electrode's running impedance average may be compared to its baseline. If a change in impedance reading, from the baseline, exceeds a threshold (which may be user, vendor, and/or manufacturer customizable), the electrode is identified as being located within the introducer sheath. The electrodes' individual in-sheath statuses may then undergo spatial and temporal verification. For example, if an electrode is determined to be within the sheath, then all electrodes proximal to the electrode must also be in the sheath. Conversely, if an electrode is determined to be out of the sheath, all electrodes distal of the electrodes must also be out of the sheath. If several electrodes share a common location along a longitudinal axis of the catheter, then all of these common electrodes must have the same in-sheath status (see, e.g., FIG. 5). Finally, the electrodes of the catheter enter/exit the introducer sheath in sequence (assuming a sufficient sampling frequency for sheath detection compared to relative velocity of the catheter to the introducer sheath). For example, if the previous time period sampling of electrode impedance data leads to the determination that 6 electrodes of 12 were within the sheath, then a next sampling period will likely result in between 5-7 electrodes being determined as being within the sheath. By applying these rules to a sheath detection algorithm, a catheter localization and visualization system may implement accurate sheath visualization.

Figure 4A:
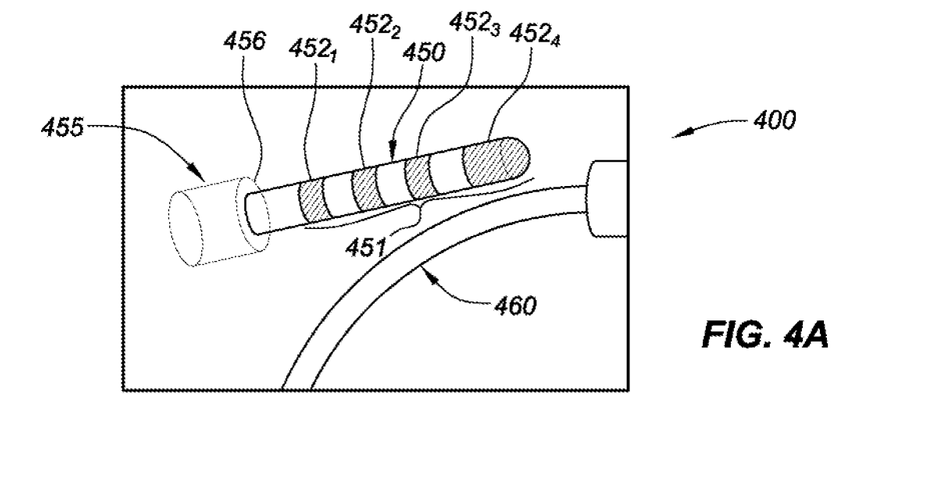
FIG. 4A shows a graphical user interface of a catheter localization and visualization system including a real-time indication of a therapeutic catheter extending out of an introducer sheath's distal end overlaid on a fluoroscopic image of a patient's vasculature, consistent with various embodiments of the present disclosure.

FIG. 4A shows a graphical user interface 400 of a catheter localization and visualization system, including a fluoroscopic image of a patient's vasculature with a real-time indication of a therapeutic (EP) catheter 450, extending out of a distal end 456 of introducer sheath 455, overlaid on the fluoroscopic image. Background elements of the fluoroscopic image have been removed for clarity. FIG. 4A further shows an adjacent catheter 460 which is located in proximity to the EP catheter 450 and may perform diagnostics or other tasks in support of the EP catheter 450.

In FIG. 4A, GUI 400 shows a distal tip region 451 of catheter 450 fully extended out of introducer sheath 455. During operation of a sheath detection algorithm, in accordance with the present disclosure, electrical signals from each of electrodes $452_{1-4}$ may be monitored by controller circuitry. The controller circuitry monitors impedance from the electrodes and compares the (near) real-time impedance measurements to baseline impedance measurements. As shown in FIG. 4A, the controller circuitry has determined that the impedance measurements of all the electrodes are below a threshold indicative of sheath contact. Accordingly, the controller circuitry visualizes the relative position of the sheath, in the GUI, as being proximal to a distal tip region 451 of the catheter 450. When all the electrodes are determined to be outside the sheath, the controller circuitry may no longer know the actual location of the tip of the sheath, only that it is somewhere proximal to the electrodes 452.

Figure 4B:
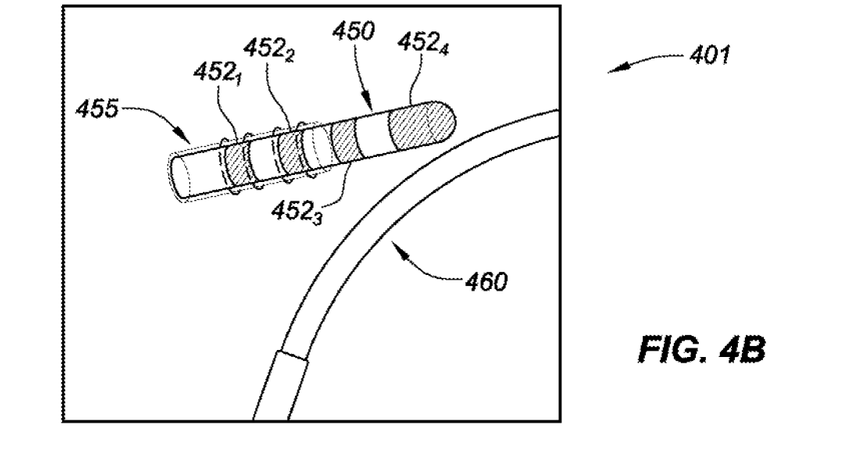
FIG. 4B shows a graphical user interface of a catheter localization and visualization system including a real-time indication of a therapeutic catheter extending partially out of an introducer sheath's distal end overlaid on a fluoroscopic image of a patient's vasculature, consistent with various embodiments of the present disclosure.

FIG. 4B shows a graphical user interface 401 of a catheter localization and visualization system including a fluoroscopic image of a patient's vasculature with a real-time visualization of an EP catheter 450, extending partially out of a distal end of an introducer sheath 455, overlaid on the fluoroscopic image. Background elements of the fluoroscopic image have been removed for clarity. FIG. 4B further shows an adjacent catheter 460 which is located in proximity to the EP catheter 450 and may perform diagnostics or other tasks in support of the EP catheter 450.

During operation of a sheath detection algorithm, in accordance with the present disclosure, electrical signals from each of electrodes $452_{1-4}$ may be monitored by controller circuitry. In the particular case visualized in FIG. 4B, the controller circuitry detects an impedance above a threshold amount in electrodes $452_{1-2}$, indicative of catheter sheath contact. However, the sensed impedances at electrodes $452_{3-4}$ are (at or) near the baseline readings, indicating a non-sheath contact state. Accordingly, the controller circuitry displays the catheter 450, in the GUI 401, as partially extending out of the introducer sheath 455, with a distal end of the introducer sheath located between electrode $452_2$ and electrode $452_3$.

Figure 4C:
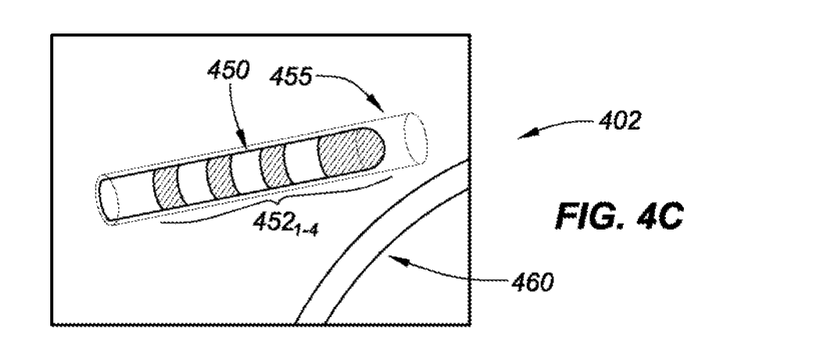
FIG. 4C shows a graphical user interface of a catheter localization and visualization system including a real-time indication of a therapeutic catheter entirely within an introducer sheath's distal end overlaid on a fluoroscopic image of a patient's vasculature, consistent with various embodiments of the present disclosure.

FIG. 4C shows a GUI 402 of a catheter localization and visualization system including a fluoroscopic image of a patient's vasculature with a real-time visualization of an EP catheter 450, entirely within an introducer sheath 455, overlaid on the fluoroscopic image. Similar to FIGS. 4A and 4B, background elements of the fluoroscopic image have been removed for clarity, and FIG. 4C further shows an adjacent catheter 460 which is located in proximity to the EP catheter 450 and may perform diagnostics or other tasks in support of the EP catheter 450.

In FIG. 4C, controller circuitry, running a sheath detection algorithm, has determined that the electrical impedance sensed at each of the electrodes $452_{1-4}$ exceeds a threshold (indicative of sheath contact). As a result, the controller circuitry concludes that the entire catheter 450 is enclosed within the sheath 455. Accordingly, the controller circuitry displays a visualization on the GUI 402 (as shown in FIG. 4C) of the catheter 450 within the visualized introducer sheath. The visualization of the introducer sheath in the GUI is particularly relevant for a clinician as a real-time fluoroscopic image of the operating region may not provide a (sufficient) visual verification of the relative location of the introducer sheath relative to the catheter. Moreover, the visualization of the introducer sheath 455 facilitates the clinician's understanding of the EP catheter's position relative to target tissue.

As in FIG. 4C, where all the electrodes 452 are within sheath 455, the controller circuitry may no longer know the actual location of a distal tip of the sheath, only that the distal tip of the sheath is distal all the electrodes of the catheter.

Figure 5A:
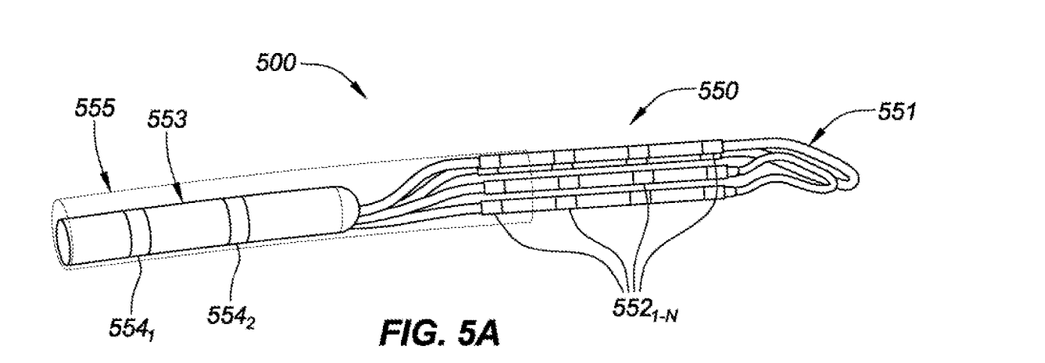
FIG. 5A is an isometric side view of a planar array catheter partially extending out of an introducer sheath, consistent with various embodiments of the present disclosure.
Figure 5B:
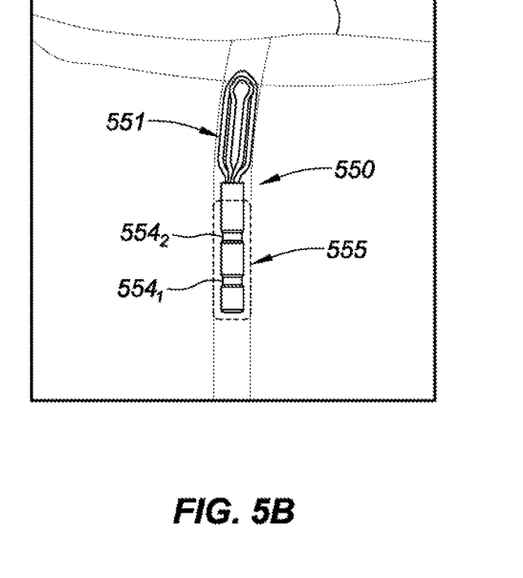
FIG. 5B shows a graphical user interface of a catheter localization and visualization system including a real-time indication of a diagnostic catheter entirely within an introducer sheath's distal end overlaid on a fluoroscopic image of a patient's vasculature, consistent with various embodiments of the present disclosure.
Figure 5C:
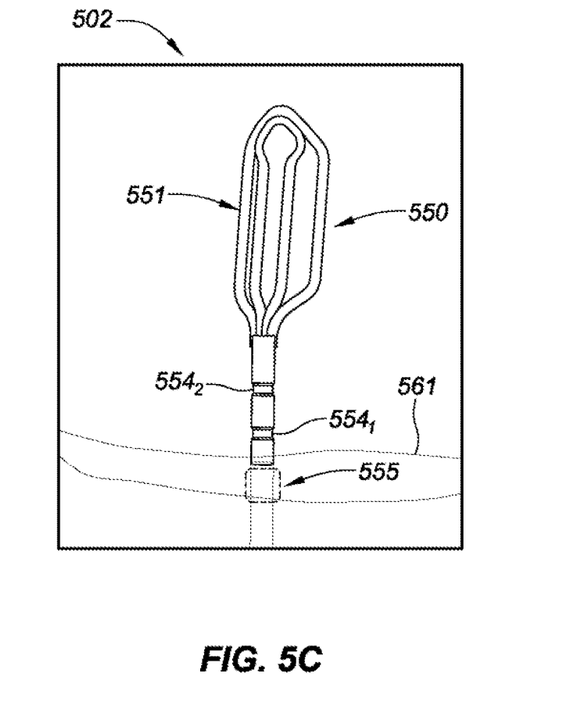
FIG. 5C shows a graphical user interface of a catheter localization and visualization system including a real-time indication of a diagnostic catheter extending entirely out of an introducer sheath's distal end overlaid on a fluoroscopic image of a patient's vasculature, consistent with various embodiments of the present disclosure.

Aspects of sheath detection and visualization may also be readily applied to planar array type catheters, as discussed further in reference to FIGS. 5A-C.

FIG. 5A is an isometric side view of an intravascular catheter system 500 including a planar array catheter 550 and an introducer sheath 555. As shown in FIG. 5A, the planar array catheter is partially extending out of the introducer sheath. FIG. 5A may be presented to a clinician as a visualization of an intravascular position of the planar array catheter 550 relative to the introducer sheath 555, via a GUI. While the intravascular position of the planar array catheter may be readily determined by virtue of the localization sensors embedded thereon (e.g., magnetic and/or impedance based sensors), the introducer sheath 555 may not be compatible with one or more localization and navigation systems and/or may not include the necessary sensors. Moreover, clinician examination of real-time fluoroscopic imaging may not reliably and repeatedly detect a distal most end of the sheath 555, as the sheath may be obscured by the catheter shaft 553. Accordingly, aspects of the present disclosure are directed to sheath detection and visualization utilizing the sensors embedded on the catheter 550 paired with the introducer sheath 555. In the present embodiment, ring electrodes $554_{1-2}$ on catheter shaft 553, and/or EP electrodes $552_{1-N}$ on planar array 551, may be monitored in an effort to detect a change of impedance as the catheter traverses through introducer sheath 555 indicative of (non-)contact with the inner wall of the sheath.

FIG. 5B shows a GUI 501 of a catheter localization and visualization system including a fluoroscopic image of a patient's vasculature with a real-time indication of a diagnostic catheter 550 entirely within an introducer sheath 555 overlaid on the fluoroscopic image. As shown in FIG. 5B, a planar array 551, at a distal end of the catheter 550, is contracted as it traverses a length of the introducer sheath. The introducer sheath in the present GUI visualization has punctured through a fossa ovalis 561 (via a transseptal puncture), and has been anchored thereto. Accordingly, a distal tip of the introducer sheath facilitates access to a left atrium of a cardiac muscle. To facilitate a clinician's understanding of a planar array 551 position relative to the introducer sheath 555, controller circuitry for the navigation and visualization system may run a sheath detection algorithm to determine this relative position. In the present embodiment, the controller circuitry has determined that ring electrodes $554_{1-2}$ are in contact with an inner wall of the sheath. Accordingly, the introducer sheath 555 is visualized in the GUI as extending distal of the ring electrodes. As illustrated by the present embodiment, and further in FIG. 5C, it is desirable for a clinician to understand when the planar array 551 of the catheter has exited the introducer sheath 555. In the present example, upon exiting the introducer sheath the planar array is positioned within the left atrium of the cardiac muscle and may be steered into position with target tissue (e.g., pulmonary venous tissue) for diagnostics and therapy. Premature steering inputs to the catheter while the planar array remains within the introducer sheath may damage the catheter, introducer sheath, and/or the patient's vasculature.

The dotted box in FIG. 5B is an overlay that is intended to indicate to the clinician a distal most end of the introducer sheath 555. In the present embodiment, electrodes on the planar array 551 are not also utilized for sheath detection and therefore the furthest point for which the controller circuitry can detect contact with the introducer sheath 555 is the distal most ring electrode (e.g., ring electrode $554_2$).

FIG. 5C shows a GUI 502 of a catheter localization and visualization system including a fluoroscopic image of a patient's vasculature with a real-time indication of a planar array 551 and ring electrodes $554_{1-2}$ of a diagnostic catheter 550 extending entirely out of an introducer sheath 555. The resulting catheter and introducer sheath visualizations are overlaid on the fluoroscopic image. Similar to FIG. 5B, the introducer sheath is anchored to a fossa ovalis 561 and the distal end of the introducer sheath is visualized as dotted box 555. Based on the teachings of the present disclosure, the distance from the electrodes to the magnetic sensor may be determined, and used to visualize the approximate position of the diagnostic catheter relative to the distal end of the introducer sheath.

In the present embodiment, the proximal most point along the catheter shaft which may be utilized for sheath detection is proximal ring electrode $554_1$. Therefore, the dotted box indicates the furthest most distal point for which the distal end of the introducer sheath 555 may extend (without being detected by the proximal most ring electrode).

While FIGS. 5A-C are directed toward a planar array with four splines, various other planar array configurations are readily envisioned, as well as the number of electrodes on each spline. For purposes of sheath detection and visualization, it may be desirable to increase the number of electrodes along the length of the splines (or shaft) to improve the accuracy of the GUI visualization of the catheter relative to the introducer sheath. Moreover, while various embodiments of the present disclosure are discussed in reference to linear and planar array catheters, various other types of catheters may be readily adapted for use with a sheath detection system; for example, basket and balloon type catheters, among others.

U.S. Pat. Nos. 8,265,745 and 9,026,196 and U.S. publication no. 2016-0324441 are related to catheter sheath detection and visualization, and are hereby incorporated by reference as though fully set forth herein.

In various embodiments of the present disclosure, various states of visualization are disclosed including: a first visualization state where a visual indicator of an introducer sheath is shown proximal to a proximal-most electrode of a catheter; a second visualization state with a different visual indicator in which the sheath is disposed over at least one of the plurality of electrodes on the catheter; and a third visualization state with a third visual indicator in which the visual indicator is shown covering all of the electrodes of the catheter. Aspects of the present disclosure are also directed to controller circuitry or a computer module which monitors and tracks the states of a catheter over a period of time. In more specific embodiments, a visualization may indicate, for example, in the second visualization state a visualization of the catheter which is indicative of the type of catheter (e.g., diagnostic catheter, therapeutic/ablation catheter, planar array, linear catheter, balloon, basket catheter, etc.). Moreover, the visualization system may further indicate characteristics of the catheter via color, texture, shading, etc. on the visualization of the catheter or introducer.

While discussed in reference to applications such as atrial fibrillation, the catheter systems described herein may find application in epicardial and/or endocardial applications, and more specifically for treating symptoms associated with Brugada syndrome. For example, the catheter system may be used in epicardial procedures where the end effector is positioned between the myocardial surface and the pericardium. Alternatively, the end effector may be used in an endocardial procedure to sweep and/or analyze the inner surfaces of the myocardium and create high-density maps of the heart tissue's electrical properties.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system for visualizing an introducer sheath location within the body, the system comprising:
    controller circuitry configured and arranged to
        receive electrical signals from one or more electrodes on an electrophysiology catheter indicative of a position and orientation of a distal end of the catheter and a position of an introducer sheath relative to the catheter,
        determine the position and orientation of the distal end of the catheter and the position of the introducer sheath relative to the catheter, and
        generate an image for a display that visualizes states indicative of the relative locations of the catheter and the introducer sheath including a first visualization state where the visual indicator of the introducer sheath is proximal a proximal-most electrode of the plurality of electrodes, a second visualization state where the visual indicator of the introducer sheath is disposed over at least one of the plurality of electrodes of the catheter, and a third visualization state where the visual indicator covers each of the one or more electrodes on the catheter.

2. The system of claim 1, wherein the controller circuitry is further configured and arranged to determine the position of the introducer sheath relative to the catheter by
    determining a baseline impedance of the one or more electrodes outside of an introducer sheath,
    monitoring the impedance of the electrodes during an operation,
    determining whether the impedance of the one or more electrodes exceeds the baseline impedance, and
    generating the image for the display including the introducer sheath in one of the three visualization states based on the determined impedance of the one or more electrodes relative to the baseline impedance.

3. The system of claim 2, wherein the controller circuitry is further configured and arranged to generate the image for the display including the introducer sheath in the third visualization state when the impedance of all the monitored electrodes exceeds the baseline impedance.

4. The system of claim 2, wherein the controller circuitry is further configured and arranged to generate the image for the display including the introducer sheath in the second visualization state when the impedance of at least one of the monitored electrodes exceeds the baseline impedance.

5. The system of claim 2, wherein the controller circuitry is further configured and arranged to generate the image for the display including the introducer sheath in the first visualization state when the impedance of all the monitored electrodes is below the baseline impedance.

6. The system of claim 2, wherein the controller circuitry is further configured and arranged to vary the generated image visualizing the introducer sheath depending on the type of the catheter.

7. The system of claim 1, wherein the one or more electrodes are configured and arranged to facilitate electrophysiology mapping, catheter localization using an impedance-based navigation system, or catheter localization using a magnetic field based navigation system.

8. The system of claim 2, wherein the controller circuitry is further configured and arranged to verify introducer sheath position relative to the catheter using geometric and temporal rules, including:
    the electrodes determined to be out of the sheath are contiguous and include the distal most electrode on the catheter and the electrodes determined to be in the sheath are contiguous and include the proximal most electrode on the catheter, and
    during relative movement between the catheter and the introducer sheath, the electrode impedance readings cross the impedance threshold sequentially based on relative position along a length of the catheter.

9. The system of claim 1, wherein the generated image for the display is overlaid on a real-time fluoroscopic image, three-dimensional model, or a static fluoroscopic image.

10. A system for detecting and visualizing a location of an introducer sheath comprising:
    an introducer sheath configured and arranged to navigate a patient vasculature;
    a catheter including one or more electrodes, the catheter configured and arranged to be delivered to a target region within the vasculature via a lumen within the introducer sheath;
    controller circuitry communicatively coupled to the one or more electrodes and configured and arranged to
        determine a position of the catheter within the patient based on electrical signals received from the one or more electrodes on the catheter,
        determine an approximate position of the introducer sheath based on the electrical signals received from the one or more electrodes on the catheter, and
        generate an image for a display that visualizes the relative locations of the catheter and the introducer sheath; and the display, communicatively coupled to the controller circuitry, is configured and arranged to display the generated image to a clinician to assist in diagnostic and therapeutic intravascular procedures.

11. The system of claim 10, wherein the controller circuitry is further configured and arranged to determine the position of the introducer sheath relative to the catheter by determining a baseline impedance of the one or more electrodes outside of an introducer sheath and monitoring the impedance of the electrodes during an operation, when the impedance of one or more of the electrodes exceeds a threshold, the one or more electrodes are determined to be in contact with an inner wall of the catheter sheath.

12. The system of claim 11, wherein the controller circuitry is further configured and arranged to generate an image visualizing the catheter enclosed within the introducer sheath when the impedance of all the monitored electrodes exceeds the threshold.

13. The system of claim 11, wherein the controller circuitry is further configured and arranged to generate an image visualizing the catheter partially enclosed within the introducer sheath when the impedance of at least one of the monitored electrodes exceeds the threshold.

14. The system of claim 11, wherein the controller circuitry is further configured and arranged to visualize a distal end of the introducer sheath extending past the electrodes on the catheter in response to sensing electrical signals indicative of sheath contact.

15. The system of claim 11, wherein the controller circuitry is further configured and arranged to generate an image visualizing an end effector of the catheter extending out of a distal end of the introducer sheath when the impedance of the one or more monitored electrodes are below the threshold.

* * * * *